United States Patent [19]

Klein et al.

[11] 4,137,311

[45] Jan. 30, 1979

[54] SYNERGISTIC COMPOSITIONS AND METHOD OF USE

[75] Inventors: Robert W. Klein, Blue Bell; George W. Nuss, Jr., Lansdale, both of Pa.

[73] Assignee: William H. Rorer, Inc., Fort Washington, Pa.

[21] Appl. No.: 835,596

[22] Filed: Sep. 22, 1977

[51] Int. Cl.$^2$ ............................................. A61K 31/56
[52] U.S. Cl. ..................................... 424/240; 424/263
[58] Field of Search ..................... 260/397.45; 424/240

[56] References Cited

U.S. PATENT DOCUMENTS 4,048,310  9/1977  Chen et al. ............................ 424/240

*Primary Examiner*—Ethel G. Love

[57] ABSTRACT

The present invention relates to a novel synergistic composition and to a method of treating inflammation in warm blooded animals by topically administering to a warm blooded animal in need of such treatment an effective amount of the synergistic combination of a corticosteroid and at least one adduct of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2.

18 Claims, No Drawings

SYNERGISTIC COMPOSITIONS AND METHOD OF USE

BACKGROUND OF THE INVENTION

The present invention relates to the novel method of treating inflammation in mammals by administering the synergistic combination of a corticosteroid and at least one metal salt of bis-(2-pyridyl-1-oxide) disulfide and to novel compositions containing such compounds.

Bis-(2-pyridyl-1-oxide) disulfide (also referred to as 2,2'-dithiodipyridine-1–1'-dioxide) and various derivatives thereof, have previously been disclosed in the literature. For example, U.S. Pat. No. 2,742,476 discloses bis-(2-pyridyl-1-oxide) disulfide and the lower alkyl substituted derivatives thereof. U.S. Pat. No. 3,027,371 discloses molybdate derivatives, U.S. Pat. No. 3,027,732 discloses stannous chloride derivatives, and U.S. Pat. No. 3,346,578 discloses stannous fluoride derivatives of bis-(2-pyridyl-1-oxide) disulfide and each refer to the anti-fungal and antibacterial properties of said derivatives.

U.S. Pat. No. 3,890,434 discloses hair and antiseptic formulations containing adducts of bis-(2-pyridyl-1-oxide) disulfide with alkaline earth metal salts.

Co-pending application Ser. No. 835,594, of R. W. Klein relates to the treatment of inflammation through the use of the metal salts of bis-(2-pyridyl-1-oxide) disulfide.

DETAILED DESCRIPTION OF THE INVENTION

Now it has been found that even more pronounced pharmacological properties for the relief and inhibition of inflammation conditions can be provided by the topical administration of the combination of a corticosteroid and the adducts of bis-(2-pyridyl-1-oxide) disulfide according to this invention. More specifically, these adducts have the formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2. More particularly, the anion Y is selected from the group consisting of halides, sulfates, nitrates, chlorates and acetates, with the chlorides and sulfates being most preferable. More particularly preferred are the water soluble adducts, especially calcium chloride ($CaCl_2$) or magnesium sulfate ($MgSO_4$). Also included in the adducts of this invention are the hydrates of the aforementioned compounds, i.e., adducts including $nH_2O$ groups where n is an integer of 0 to 10. Additionally, the adducts (I) may contain one or more substituents on either or both pyridine ring structures such as alkyls, halogens and alkoxy groups. It is further noted that $(C_5H_4NOS)_2$ as used in (I) above and throughout the specification and claims represents bis-(2-pyridyl-1-oxide) disulfide and the structural formula shown as follows:

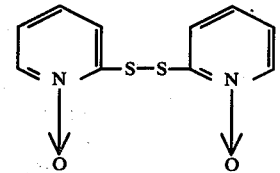

Among the active ingredients which may be utilized in combination with corticosteroids in this invention may be mentioned:

Bis-(2-pyridyl-1-oxide) disulfide magnesium sulfate, bis-(2-pyridyl-1-oxide) disulfide magnesium acetate, bis-(2-pyridyl-1-oxide) disulfide magnesium chloride, bis-(2-pyridyl-1-oxide) disulfide magnesium bromide, bis-(2-pyridyl-1-oxide) disulfide calcium chloride, bis-(2-pyridyl-1-oxide) disulfide calcium sulfate, bis-(2-pyridyl-1-oxide) disulfide calcium nitrate, bis-(2-pyridyl-1-oxide) disulfide calcium acetate, bis-(2-pyridyl-1-oxide) disulfide calcium chlorate, bis-(2-pyridyl-1-oxide) disulfide barium chloride, bis-(2-pyridyl-1-oxide) disulfide barium sulfate, bis-(2-pyridyl-1-oxide) disulfide barium nitrate, bis-(2-pyridyl-1-oxide) disulfide barium acetate, bis-(2-pyridyl-1-oxide) disulfide barium chlorate, bis-(2-pyridyl-1-oxide) disulfide strontium chloride, bis-(2-pyridyl-1-oxide) disulfide strontium sulfate, bis-(2-pyridyl-1-oxide) disulfide strontium nitrate, bis-(2-pyridyl-1-oxide) disulfide strontium acetate, bis-(2-pyridyl-1-oxide) disulfide strontium chlorate, bis-(2-pyridyl-1-oxide) disulfide potassium chloride, bis-(2-pyridyl-1-oxide) disulfide potassium sulfate, bis-(2-pyridyl-1-oxide) disulfide potassium nitrate, bis-(2-pyridyl-1-oxide) disulfide potassium acetate, bis-(2-pyridyl-1-oxide) disulfide potassium chlorate, bis-(2-pyridyl-1-oxide) disulfide sodium chloride, bis-(2-pyridyl-1-oxide) disulfide sodium sulfate, bis-(2-pyridyl-1-oxide) disulfide sodium nitrate, bis-(2-pyridyl-1-oxide) disulfide sodium acetate, bis-(2-pyridyl-1-oxide) disulfide sodium chlorate, bis-(2-pyridyl-1-oxide) disulfide zinc chloride, bis-(2-pyridyl-1-oxide) disulfide zinc sulfate, bis-(2-pyridyl-1-oxide) disulfide zinc nitrate, bis-(2-pyridyl-1-oxide) disulfide zinc acetate, bis-(2-pyridyl-1-oxide) disulfide zinc chlorate, bis-(2-pyridyl-1-oxide) disulfide stannous chloride, bis-(2-pyridyl-1-oxide) disulfide stannous sulfate, bis-(2-pyridyl-1-oxide) disulfide stannous nitrate, bis-(2-pyridyl-1-oxide) disulfide stannous acetate, bis-(2-pyridyl-1-oxide) disulfide stannous chlorate, bis-(2-pyridyl-1-oxide) disulfide zirconium chloride, bis-(2-pyridyl-1-oxide) disulfide zirconium sulfate, bis-(2-pyridyl-1-oxide) disulfide zirconium nitrate, bis-(2-pyridyl-1-oxide) disulfide zirconium acetate, bis-(2-pyridyl-1-oxide) disulfide zirconium chlorate, bis-(2-pyridyl-1-oxide) disulfide ferrous chloride, bis-(2-pyridyl-1-oxide) disulfide ferrous sulfate, bis-(2-pyridyl-1-oxide) disulfide ferrous nitrate, bis-(2-pyridyl-1-oxide) disulfide ferrous acetate, bis-(2-pyridyl-1-oxide) disulfide ferrous chlorate, bis-(2-pyridyl-1-oxide) disulfide lithium chloride, bis-(2-pyridyl-1-oxide) disulfide lithium sulfate, bis-(2-pyridyl-1-oxide) disulfide lithium nitrate, bis-(2-pyridyl-1-oxide) disulfide lithium acetate, and bis-(2-pyridyl-1-oxide) disulfide lithium chlorate.

Any one of the known effective anti-inflammatory corticosteroids may be utilized in this invention. Among the suitable corticosteroids include hydrocortisone, hydrocortisone acetate, hydrocortisone butyrate, hydrocortisone valerate, triamcinolone acetonide, fluocinolone acetonide, 16α-hydroxyprednisolone-16α, 17-acetonide, fluorohydrocortisone, 1-dehydrocortisone, and the like. Preferably, the hydrocortisone compounds are used in connection with the active adducts I.

In accordance with the present invention, a method of treating inflammation in warm blooded animals is provided which comprises topically administering to a warm blooded animal in need of such treatment an effective amount of the combination of a corticosteroid and the adducts of Formula I.

As used herein, the term "treatment" is meant to include both active treatment and preventative or prophylactic treatment.

Additionally, the effective compounds utilized in the present invention have been shown to have the property of remaining on the skin and retaining anti-inflammatory activity over a period of time after washing and rinsing of the skin.

The present invention has for its object compositions and means for treating skin conditions requiring anti-inflammatory treatment such as contact dermatitis, seborrheic dermatitis, atopic dermatitis, neuro dermatitis and the like, a composition containing the combination of a corticosteroid and at least one of adducts I in an amount of from about 0.05 to 5.0% by weight of the composition, preferably from 0.1 to 1.0% by weight. The corticosteroids are utilized in the composition in an amount of 0.01–2.5% by weight of adduct I in the composition preferably 0.1–1% by weight of adduct I present. These compositions can be in the form of a solution, a cream, powder, gel, ointment, salve, lotion, or milk. They can also constitute make-up products or dermatological cakes containing the ingredients standard to this type of composition.

The following examples will further illustrate the formulations containing the corticosteroids and the adducts (I) but are not to be considered as limiting the scope of this invention.

EXAMPLE 1

Testing of the synergistic effect of the combination of hydrocortisone and the adducts of Formula I, using as a representative compound bis-(2-pyridyl-1-oxide) disulfide magnesium sulfate was performed utilizing a modification of the experimental technique described by Tonelli, G., Thibault, L. and Ringler, L., A Bioassay for the Concomitant Assessment of the Anti-phlogistic and Thymolytic Activities of Topically Applied Corticoids. Endocrinology 77,625 (1965) and Roszkowski, A. P., Rooks, W. H. II, Tomolonis, A. J. and Miller, L. M., Anti-inflammatory and Analgetic Properties of d-2-(6'Methoxy-2'-Naphthyl) Propionic Acid (Naproxen). J. Pharm. Exp. Ther. 179,114 (1971). Mathematical determination of the synergistic effects of combinations of bis-(2-pyridyl-1-oxide) disulfide magnesium sulfate and hydrocortisone was done using a modification of the method described by Van Arman, C. G., Nuss, G. W. and Risley. E. A., Interactions of Aspirin, Indomethacin and Other Drugs In Adjuvant-induced Arthritis In The Rat (appendix). J. Pharmacol, Exp. Therap. 187, 400, (1973).

Hydrocortisone and bis-(2-pyridyl-1-oxide) disulfide magnesium sulfate were suspended or dissolved in ethanol U.S.P. (200 proof) at concentrations of 20, 40 and 80 mg/ml of bis-(2-pyridyl-1-oxide) disulfide magnesium sulfate and 0.01, 1 and 10 mg of hydrocortisone. In experiments where the interaction of hydrocortisone and bis-(2-pyridyl-1-oxide) disulfide magnesium sulfate were to be determined, equipotent doses of each agent were simultaneously co-applied after admixture in the alcohol vehicle. Bis-(2-pyridyl-1-oxide) disulfide magnesium sulfate formed a fine suspension, while hydrocortisone was completely soluble in the alcohol.

Therapeutic effects of bis-(2-pyridyl-1-oxide) disulfide magnesium sulfate at topical doses of 2, 4 and 8 mg/ear (0.01 ml) of hydrocortisone at doses of 0.01, 0.1 and 1 mg/ear (0.1 ml) were measured after application to the left ear of mice, 1 hour after inflammation was induced by the topical application of an irritant solution containing 2% croton oil (Amend Drug and Chemical Co., Irvington, N.J. Lot 710034), 73% diethyl ether, U.S.P. (Corco Chemical Corp., Fairless Hills, PA), 20% pyridine (J. T. Baker Chemical Co., Phillipsburg, PA, Lot 3348) and 5% distilled water. Groups of mice treated with only the croton oil irritant solution served as controls. The right ear of mice in any group was not treated.

Four hours after application of the irritant vehicle (three hours after drug application) both ears were amputated and one circular section was exercised from each ear using a No. 4 cork borer (7 mm i.d.). The ear sections were then weighed. The increase in weight due to edema formation caused by the croton oil in the treated ear and reduction of the edema caused by treatment with bis-(2-pyridyl-1-oxide) disulfide magnesium sulfate hydrocortisone or combinations thereof was determined by subtracting the weight of the untreated right ear section from that of the treated left ear section.

The anti-inflammatory effects of either bis-(2-pyridyl-1-oxide) disulfide magnesium sulfate or hydrocortisone or of co-applied equipotent dose pair combinations of the two agents expressed as percent inhibition were calculated by:

$$\frac{\text{Edema weight (controls)} - \text{Edema weight (treated)}}{\text{Edema weight (controls)}} \times 100$$

The immediate anti-inflammatory effects of bis-(2-pyridyl-1-oxide) disulfide magnesium sulfate were measured by direct application to the ear of the drug suspended in a 2% solution of croton oil in 95% ethanol. Ethanol was used as the vehicle; pyridine contained in the usual irritant vehicle as described previously produces an alkaline reaction. Controls were treated with only the croton oil vehicle.

The potential synergistic effects induced by topical co-application of doses of hydrocortisone and bis-(2-pyridyl-1-oxide) disulfide magnesium sulfate were investigated by both immediate application (Table I) and by delayed application to an existing inflammation (Table II).

A. Synergism after Immediate Application

A fixed dose of 4 mg/ear of bis-(2-pyridyl-1-oxide) disulfide magnesium sulfate was co-applied with 0.01, 0.1 and 1 mg/ear of hydrocortisone. Such co-application at the time of induction of the inflammatory process (Table I) resulted in effects that were less than those which would be expected from simple addition, i.e., there was evidence that some antagonism of therapeutic effects occurred under these conditions. At the dose of 0.01 mg/ear, hydrocortisone produced 53.3% inhibition. When that same dose of hydrocortisone was co-applied with 4 mg/ear of bis-(2-pyridyl-1-oxide) disulfide magnesium sulfate (24.9% inhibition by itself), a response of only 39.6% was obtained; a response of 58.5% inhibition was expected. This reduction in response obtained after coapplication of combinations of bis-(2-pyridyl-1-oxide) disulfide magnesium sulfate and hydrocortisone was evident at all dose levels.

B. Synergism after Delayed Application

When equipotent dose-pair combinations of bis-(2-pyridyl-1-oxide) disulfide magnesium sulfate and hydrocortisone were co-applied to an existing inflammation in the mouse's ear, the results in Table II were obtained. The observed responses at each dose level of the combinations were compared with the expected responses calculated on the basis of simple addition. The type of interaction between bis-(2-pyridyl-1-oxide) disulfide magnesium sulfate and hydrocortisone was dose-dependent and varied from potentiation to simple addition.

Doses of bis-(2-pyridyl-1-oxide) disulfide magnesium sulfate (0.87 mg/ear) and hydrocortisone (0.00125 mg/ear) ech by themselves would be expected, by extrapolation of their respective dose-response lines, to produce little, if any, significant anti-inflammatory response. When the expected response that would result in simple addition was calculated from that dose-pair combination, a value of 10.6% inhibition was obtained; the observed response was 46.3%. In order to achieve a similar response from either hydrocortisone or bis-(2-pyridyl-1-oxide) disulfide magnesium sulfate by themselves, it would have been necessary to apply 0.25 mg/ear or 17.7 mg/ear, respectively.

Similar potentiation was observed with combinations of bis-(2-pyridyl-1-oxide) disulfide magnesium sulfate 1/5 mg/ear and hydrocortisone 0.004 mg/ear, or bis-(2-pyridyl-1-oxide) disulfide magnesium sulfate 1.9 mg/ear and hydrocortisone 0.005 mg/ear. Higher doses of bis-(2-pyridyl-1-oxide) disulfide magnesium sulfate in combination with equipotent doses of hydrocortisone resulted in simple addition.

TABLE

The Interaction of Bis-(2-Pyridyl-1-Oxide) Disulfide Magnesium Sulfate With Hydrocortisone After Immediate CO-Administration To Croton-Oil Induced Inflammation To The Mouse's Ear

| Treatment[a] | Topical Dose mg/ear | Edema Weight mg ± S.D.[b] | Percent Inhibition of Ear Edema |
| --- | --- | --- | --- |
| Control | — | 16.9±3.0 | — |
| Bis-(2-pyridyl-1-oxide) disulfide magnesium sulfate | 4 | 12.7±3.0 | 24.9 |
| Hydrocortisone | 0.01 | 13.0±3.8 | 23.1 |
|  | 0.1 | 7.9±2.3 | 53.3 |
|  | 1.0 | 5.5±2.6 | 67.5 |
| Bis-(2-pyridyl-1-oxide) disulfide magnesium sulfate | 4 | 14.3±2.2 | 15.4 |
| Hydrocortisone | 0.01 |  |  |
| Bis-(2-pyridyl-1-oxide) disulfide magnesium sulfate | 4 | 10.2±2.6 | 39.6 |
| Hydrocortisone | 0.1 |  |  |
| Bis-(2-pyridyl-1-oxide) disulfide magnesium sulfate disulfide magnesium sulfate | 4 | 8.4±2.1 | 50.3 |
| Hydrocortisone | 1.0 |  |  |

[a]2% Croton oil in 95% ethanol as irritant; bis-(2-pyridyl-1-oxide) disulfide magnesium sulfate alone or bis-(2-pyridyl-1-oxide) disulfide magnesium sulfate and hydrocortisone suspended in the same vehicle.
[b]Standard Deviation.

TABLE II

The Interaction of Bis-(2-Pyridyl-1-Oxide) Disulfide Magnesium Sulfate With Hydrocortisone After Delayed CO-Application to Croton-Oil Induced Inflammation to The Mouse's Ear

| Treatment[a] | Topical Dose mg/ear | Ear Edema Weight mg ± S.D.[b] | Percent Inhibition of Ear Edema |
| --- | --- | --- | --- |
| Control | — | 14.9±3.8 |  |
| Bis-(2-pyridyl-1-oxide) disulfide magnesium sulfate | 2 | 12.7±2.4 | 14.8 |
|  | 4 | 11.4±2.8 | 23.5 |
|  | 8 | 9.6±2.2 | 35.6 |
| Hydrocortisone (free alcohol) | 0.01 | 12.3±3.3 | 17.5 |
|  | 0.1 | 8.9±2.3 | 40.3 |
|  | 1.0 | 6.2±2.4 | 58.4 |
| Bis-(2-pyridyl-1-oxide) disulfide magnesium sulfate | 0.87 | 7.9±2.5 | 47.3 |
| Hydrocortisone | 0.00125 |  |  |
| Bis-(2-pyridyl-1-oxide) disulfide magnesium sulfate | 1.5 | 9.2±2.7 | 38.1 |
| Hydrocortisone | 0.005 |  |  |
| Bis-(2-pyridyl-1-oxide) disulfide magnesium sulfate | 3.7 | 9.87±2.7 | 34.0 |
| Hydrocortisone | 0.004 |  |  |
| Bis-(2-pyridyl-1-oxide) disulfide magnesium sulfate | 1.9 | 9.5±2.4 | 36.4 |
| Hydrocortisone | 0.005 |  |  |
| Bis-(2-pyridyl-1-oxide) disulfide magnesium sulfate | 3.7 | 9.87±2.7 | 34.0 |
| Hydrocortisone | 0.02 |  |  |
| Bis-(2-pyridyl-1-oxide) disulfide magnesium sulfate | 7.0 | 8.7±2.4 | 41.6 |
| Hydrocortisone | 0.08 |  |  |

[a]Drug suspended or dissolved in 95% ethanol and applied 1 hour after 2% croton oil.
[b]Standard Deviation

| | |
| --- | --- |
| Bis-(2-pyridyl-1-oxide) disulfide calcium chloride | 2g |
| Hydrocortisone | 0.05g |
| Titanium oxide | 10g |
| Red iron oxide | 0.3g |
| Yellow iron oxide | 0.2g |
| Brown iron oxide | 0.4g |
| Chestnut iron oxide | 0.2g |

Several stearyl alcohols oxyethylenated with 33 of ethylene oxide 7 g

| | |
| --- | --- |
| Polyglycol stearate | 6g |
| Propyl parahydroxybenzoate | 0.2g |
| Water, Q.S.P. | 100g |

Other creams identical to that described immediately above are prepared by replacing the calcium chloride compound with any of the previously mentioned active compounds.

EXAMPLE 3

A dermatological cleansing cake is prepared by mixing together the following components:

Esters of sodium isothionate and coprafatty acids (sold under the tradename "IGEPON A") having the formula

| | |
| --- | --- |
| R—COO—CH$_2$—CH$_2$—SO$_3$Na, wherein R equals fatty acid derivatives having 12–15 carbon atoms) | 75g |
| Lanolin derivatives | 22.75g |
| (C$_5$H$_4$NOS)$_2$ . MgCl$_2$ | 2g |
| Hydrocortisone acetate | 0.02g |

Other dermatological cleansing cakes, identical to the above, are prepared by replacing the magnesium chloride salt of bis-(2-pyridyl-1-oxide) disulfide with any one of the aforementioned active compounds. Also, any one of the corticosteroid mentioned may be utilized.

EXAMPLE 4

A powder comprising the following mixture:

| | |
|---|---|
| Talc | 99.6g |
| Glycerine oleate | 3g |
| Isopropyl myristate | 7g |
| Bis-(2-pyridyl-1-oxide) disulfide magnesium sulfate | 3g |
| Hydrocortisone valerate | 0.15g |
| Perfume | 2cc |

Other equally effective powder compositions identical to the above are prepared except that the active ingredient component bis-(2-pyridyl-1-oxide) disulfide magnesium sulfate is replaced by any of the other aforementioned active compounds.

EXAMPLE 5

Cocoa butter (approximately 40g) is mixed with bis-(2-pyridyl-1-oxide) disulfide zinc acetate (approximately 1g and triamcinolone acetonide (0.05g) and the resulting mixture is melted with gentle heat and poured into a mold of suitable size and shape.

EXAMPLE 6

The following ointment base was utilized as a vehicle for the active ingredients of this invention:

| Ingredient | Amount in grams |
|---|---|
| Polyoxyethylene stearyl ether | 5.0 |
| White petrolatum | 5.0 |
| Stearyl alcohol | 15.0 |
| Distilled water | 63.5 |

The ointment containing the above active ingredients was manufactured in the following manner. 3.80 grams bis-(2-pyridyl-1-oxide) disulfide magnesium sulfate were dissolved in a heated mixture of 56.7 ml. of distilled water and 11.50g of propylene glycol. This solution was heated to a temperature of 75° C and added to a mixture having a like temperature consisting of 0.05g of hydrocortisone, 15.0g of stearyl alcohol, 5.0g of white petrolatum, 1.0ml of concentrated ammonium solution and 5.0g of polyoxyethylene stearyl ether, molecular weight about 700. While the resulting mixture was still hot, lactic acid was added to adjust the pH thereof to about 5.5 to approximate the pH of skin. The resulting mixture was thereafter cooled to form a cream which was further worked utilizing a three-roller frame and filled into tubes.

In an analogous manner, ointments with hydrocortisone were prepared utilizing the following ingredients to form the initial solutions:

a. 2.27 grams bis-(2-pyridyl-1-oxide) disulfide ferrous chloride in 53.23 ml of distilled water and 11.5g of propylene glycol;

b. 2.51 grams of bis-(2-pyridyl-1-oxide) disulfide lithium acetate in 56.19 ml of distilled water and 11.5g of propylene glycol;

c. 2.62 grams of bis-(2-pyridyl-1-oxide) disulfide zirconium chloride in 56.35 ml of distilled water and 11.5g of propylene glycol;

d. 1.0 gram of bis-(2-pyridyl-1-oxide) disulfide strontium chloride in 60.7 ml of distilled water and 11.5g of propylene glycol.

In this example the solution was heated to 75° C and added to a mixture having a like temperature and containing 2.5 grams of bis-(2-pyridyl-1-oxide) disulfide magnesium sulfate, 0.05g hydrocortisone butyrate, 13.0 grams of stearyl alcohol, 5.0 grams of polyoxyethylene stearyl ether, molecular weight about 700 and 5.0 grams of white petrolatum, the pH was adjusted with lactic acid and the mixture cooled to form a cream which was worked up as above.

EXAMPLE 7

An ointment was prepared by first mixing 1.0g of bis-(2-pyridyl-1-oxide) disulfide magnesium sulfate, 1.0g of bis-(2-pyridyl-1-oxide) disulfide magnesium chloride and 0.05g of triamcinolone acetonide in a hot mixture of 57.5g of distilled water and 11.5g of propylene glycol. The resulting mixture was heated to 75° C and added with stirring to a hot (75° C) mixture of 17.0g of stearyl alcohol, 4.0g of white petroleum jelly and 4.0g of a polyoxyethylene stearyl ether, molecular weight about 700. Lactic acid was added while the emulsion was still hot to adjust the pH thereof to a pH approximating that of skin, i.e., about 5.5. After cooling the resulting cream was further worked utilizing a three-roller frame and filled into tubes.

EXAMPLE 8

An aerosol preparation was formed from the following formulation:

| Phase I | |
|---|---|
| Ingredient | Weight in grams |
| Isopropyl myristate | 18 |
| Stearic acid, cosmetic grade | 30 |
| Myristic acid, cosmetic grade | 9 |
| Glycerin | 18 |

| Phase II | |
|---|---|
| Ingredient | Weight in grams |
| Water | 440 |
| Triethanolamine | 20 |
| Bis-(2-pyridyl-1-oxide) disulfide calcium chloride | 22 |

| Phase III | |
|---|---|
| Ingredient | Weight in grams |
| Panthenol | 6 |
| Suitable perfume | 3 |
| Fluocinoline acetonide | 0.5 |
| Lactic acid q.s. pH | 5.5 |

Phase I and Phase II were separately heated at a temperature of about 75° C. Thereafter, Phase II was added dropwise with vigorous stirring to Phase I which was maintained at a temperature of 75° C. The mixture was then cooled to above 50° C with stirring and the first three ingredients of Phase III added thereto. The resulting emulsion was mixed and the pH adjusted to about 5.5 with lactic acid. The emulsion was then cooled with stirring to about 20° C.

Nine parts by weight of the emulsion formed above were combined with one part by weight of a propellant (40 dichlorodifluoromethane/60 dichlorotetrafluoroethane) under pressure in suitable aerosol container equipped with conventional valve apparatus and foam-forming head.

EXAMPLE 9

An anti-inflammatory composition in milk form having the following composition:

| Ingredient | Weight in grams |
| --- | --- |
| Hydrogenated, ethoxylated (10 mol) lanolin | 1.8 |
| Triglyceride of fatty acid of coconut | 7.0 |
| Cetylalcohol | 0.6 |
| Stearylalcohol | 0.6 |
| Paraffin oil (lightweight) | 5.0 |
| Hydrocortisone | 0.05 |
| Stearic acid | 3.0 |
| Bis-(2-pyridyl-1-oxide) disulfide magnesium sulfate | 2.0 |
| Demineralized water | 72.2 |
| Triethanolamine | 0.8 |
| Perfume | 0.5 |
| Carboxyvinylpolymer | 2.0 |
| Conservation agent | 2.0 | was manufactured as follows:

A mixture of 1.8g hydrogenated, ethoxylated (10 mol) lanolin, 7.0g triglyceride of fatty acid of coconut, 0.6g cetylalcohol, 0.6g stearyl alcohol, 5.0g paraffin oil, 0.5g hydrocortisone and 3.0g of stearic was blended at 70° C. After addition and 2.0g bis-(2-pyridyl-1-oxide) disulfide magnesium sulfate, 2.0g carboxyvinylpolymer in 72.2g demineralized water were added at 70° C with stirring to the resulting suspension. The mixture was stirred for 15 minutes and then cooled. 0.8g of triethanolamine and 0.5g of perfume were added at 60° C and 45° C respectively. The resulting mixture was stirred until cold and a white milk, which was stable at 3,000 Rpm for 1 hour was obtained. Viscosity: 6,000 Cp (Brockfield, Spindel, 5, 10 Rpm).

EXAMPLE 10

2.5g of bis-(2-pyridyl-1-oxide) disulfide magnesium sulfate and 0.05g hydrocortisone are predispersed in 30.0g of propylene glycol. The mixture is then homogenized into 97.4 grams of finished cream, ointment or lotion following a modification of any one of the procedures of Examples 2, 6 and 7 or as described in F. W. Martin et al, "Remington's Pharmaceutical Sciences," 14th Ed., Mack Publishing Co., Easton, Pa., 1965.

Other agents which have medicinal or therapeutic value may be incorporated in the compositions of this invention.

I claim:

1. A composition for topically treating dermatitis in warm blooded animals which comprises about 0.05 to about 5% by weight of the total composition of the combination of a corticosteroid selected from the group consisting of hydrocortisone, hydrocortisone acetate, hydrocortisone butyrate, hydrocortisone valerate, triamcinolone acetonide, fluocinolone acetonide, 16α-hydroxyprednisolone-16α,17α-acetonide, fluorohydrocortisone and 1-dehydrocortisone and the adducts of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2, together with a suitable pharmaceutical carrier.

2. The composition of claim 1, wherein M is magnesium, Y is sulfate and t is 1.

3. The composition of claim 1, wherein M is calcium, Y is chloride and t is 2.

4. The composition of claim 1, wherein M is calcium, magnesium or barium.

5. The composition of claim 1, wherein the formula is selected from the group consisting of $(C_5H_4NOS)_2CaCl_2$, $(C_5H_4NOS)_2MgSO_4$, $(C_5H_4NOS)_2SrCl_2$, $(C_5H_4NOS)_2SrBr_2$, $(C_5H_4NOS)_2Ca(NO_3)_2$ and $(C_5H_4NOS)_2Ba(ClO_3)_2$.

6. The composition of claim 1, wherein said adducts are water-soluble.

7. The composition of claim 1, wherein Y is selected from the group consisting of halides, sulfates, nitrates and acetates.

8. A composition for topically treating inflammation in warm blooded animals comprising as active agents the combination of hydrocortisone and bis-(2-pyridyl-1-oxide) disulfide magnesium sulfate and a suitable pharmaceutical carrier, said active agents being present in said composition in an amount of 0.05–5% by weight of composition and said hydrocortisone being present in an amount of 0.01–2.5% by weight of bis-(2-pyridyl-1-oxide) disulfide magnesium sulfate.

9. A method of treating dermatitis in warm blooded animals which comprises topically administering to a warm blooded animal in need of such treatment an effective amount of a corticosteroid, selected from the group consisting of hydrocortisone, hydrocortisone acetate, hydrocortisone butyrate, hydrocortisone valerate, triamcinolone acetonide, fluocinolone acetonide, 16α-hydroxyprednisolone-16α,17α-acetonide, fluorohydrocortisone and 1-dehydrocortisone and at least one adduct of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2.

10. The method of claim 9, wherein M is magnesium, Y is sulfate and t is 1.

11. The method of claim 9, wherein M is calcium, Y is chloride and t is 2.

12. The method of claim 9, wherein M is calcium, magnesium or barium.

13. The method of claim 9, wherein the formula is selected from the group consisting of $(C_5H_4NOS)_2CaCl_2$, $(C_5H_4NOS)_2MgSO_4$, $(C_5H_4NOS)_2SrCl_2$, $(C_5H_4NOS)_2SrBr_2$, $(C_5H_4NOS)_2Ca(NO_3)_2$ and $(C_5H_4NOS)_2Ba(ClO_3)_2$.

14. The method of claim 9, wherein said dermatitis is contact dermatitis, seborrheic dermatitis, atopic dermatitis or neuro dermatitis.

15. The method of claim 9, wherein said adducts are water-soluble.

16. The method of claim 9, wherein Y is selected from the group consisting of halides, sulfates, nitrates and acetates.

17. The method of claim 9, wherein said corticosteroid is hydrocortisone.

18. A method for treating inflammation in warm blooded animals which comprises topically administering to a warm blooded animal in need of treatment, a pharmaceutical composition containing 0.05 to 5% by weight of the combination of hydrocortisone and bis-(2-pyridyl-1-oxide) disulfide magnesium sulfate, said hydrocortisone being present in an amount of 0.01–2.5% by weight of bis-(2-pyridyl-1-oxide) disulfide magnesium sulfate.

* * * * *

UNITED STATES PATENT AND TRADEMARK OFFICE
CERTIFICATE OF CORRECTION

PATENT NO. : 4,137,311
DATED : January 30, 1979
INVENTOR(S) : Robert W. Klein et al It is certified that error appears in the above-identified patent and that said Letters Patent are hereby corrected as shown below:

Column 5, line 23, change "ech" to --each-- line 47, change "CO" to --Co--

Column 6, line 4, change "CO" to --Co-- line 30, insert --EXAMPLE 2

A cream was prepared as follows:-- line 39, delete the line "_____"

line 41, after "33" insert --mols-- line 44, delete the line "_____"

line 60, delete the line "_____"

*Signed and Sealed this*

*Twenty-fourth* Day of *April 1979*

[SEAL]

Attest:

RUTH C. MASON
*Attesting Officer*

DONALD W. BANNER
*Commissioner of Patents and Trademarks*